United States Patent
Camden

(10) Patent No.: US 6,245,789 B1
(45) Date of Patent: *Jun. 12, 2001

(54) HIV AND VIRAL TREATMENT

(75) Inventor: James Berger Camden, West Chester, OH (US)

(73) Assignee: The Procter & Gamble Company, Cincinnati, OH (US)

(*) Notice: Subject to any disclaimer, the term of this patent is extended or adjusted under 35 U.S.C. 154(b) by 0 days.

This patent is subject to a terminal disclaimer.

(21) Appl. No.: 09/312,949

(22) Filed: May 17, 1999

Related U.S. Application Data

(63) Continuation-in-part of application No. 09/081,384, filed on May 19, 1998, now abandoned.

(51) Int. Cl.[7] .................................................. A61K 31/425

(52) U.S. Cl. ............................................................ 514/365

(58) Field of Search ...................................... 514/394, 365

(56) References Cited

U.S. PATENT DOCUMENTS

| | | | |
|---|---|---|---|
| 3,010,968 | 11/1961 | Loux ................... | 260/309.2 |
| 3,370,957 | 2/1968 | Wagner et al. ......... | 99/90 |
| 3,499,761 | 3/1970 | Dersch . | |
| 3,541,213 | 11/1970 | Klopping ............. | 424/273 |
| 3,669,969 | 6/1972 | Lunn ................. | 260/256.4 |
| 3,738,995 | 6/1973 | Adams et al. .......... | 260/309.2 |
| 3,881,014 | 4/1975 | Regel et al. .......... | 424/273 |
| 3,956,262 | 5/1976 | Heyes et al. .......... | 260/140 |
| 4,046,906 | 9/1977 | Frensch et al. ........ | 424/273 |
| 4,731,366 | 3/1988 | Munro et al. ......... | 514/278 |
| 4,814,329 | 3/1989 | Harsanyi et al. ....... | 514/396 |
| 5,098,923 | 3/1992 | Karjalainen et al. .... | 514/396 |
| 5,114,951 | 5/1992 | King ................. | 514/290 |

(List continued on next page.)

FOREIGN PATENT DOCUMENTS

| | | |
|---|---|---|
| 667158 | 11/1965 | (BE) . |
| 617968 | 10/1994 | (EP) . |
| 2155888 | 5/1973 | (FR) . |
| 07 277 956 | 10/1995 | (JP) . |
| WO 94/04541 | 3/1994 | (WO) . |
| WO 96/32103 | 10/1996 | (WO) . |
| WO 96/32104 | 10/1996 | (WO) . |
| WO 96/32107 | 10/1996 | (WO) . |
| WO 96/32115 | 10/1996 | (WO) . |
| WO 96/40119 | 12/1996 | (WO) . |
| WO 96/40120 | 12/1996 | (WO) . |
| WO 96/40122 | 12/1996 | (WO) . |
| WO 97/05870 | 2/1997 | (WO) . |
| WO 97/05872 | 2/1997 | (WO) . |
| WO 97/05873 | 2/1997 | (WO) . |
| WO 98/32440 | 7/1998 | (WO) . |
| WO 98/51303 | 11/1998 | (WO) . |
| WO 98/51304 | 11/1998 | (WO) . |
| WO 99/59585 | 11/1999 | (WO) . |

OTHER PUBLICATIONS

Delatour et al., Therapie, vol. 31, No. 4., pp. 505–515, (1976), and translation thereof.
Elgebaly et al., J. Natl. Cancer Inst., vol. 74, No. 4, pp. 811–815 (1985).
Friedman, et al., Biochimica et Biophysica Acta, 544 (1978) pp. 605–614.
Lacey, et al., Biochemical Pharma, vol. 34, No. 19, pp. 3603–3605 (1985).
Chemical Abstracts 121:175012z, (1994) p 607, Katiyar et. al.
Stedman's Medical Dictionary, 24th ed., 1983, pp./ 777–778.
Aur, J. Pediatr., 78, No. 1, (1971) pp. 129–131.
Lundy et al., Cancer Treat. Rep., vol. 62, No. 11, (1978), pp. 1955–1962.
Lundy et al., Surg. Forum, vol. 27, No. 62 (1976) pp. 132–134.
Marinovich, et al., Toxicol., vol. 94, No. 1–3, (1994) pp 173–85.

(List continued on next page.)

Primary Examiner—Jermoe D. Goldberg
(74) Attorney, Agent, or Firm—Rose Ann Dabek; Steven W. Miller

(57) ABSTRACT

A pharmaceutical composition that can be used to treat viral infections, particularly HIV. The composition comprises from about 250 mg to about 6000 mg of a benzimidazole derivative of the formula:

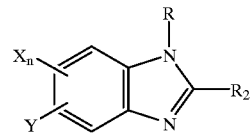

wherein X is hydrogen, halogen, alkyl of less than 7 carbon atoms or alkoxy of less than 7 carbon atoms; n is a positive integer of less than 4; Y is hydrogen, chlorine, nitro, oxychloro, methyl or ethyl; and R is hydrogen or an alkyl group having from 1 to 8 carbon atoms, and $R_2$ is 4-thiazolyl and the pharmaceutically acceptable organic or inorganic addition salts thereof. The preferred compound is thiabendazole. In the present invention it has been discovered that the compounds described above are useful for the inhibition of HIV and the treatment of HIV infection when used alone or in combination with other anti-viral agents. These compositions can prevent replication of the HIV virus, create virus resistance in the patient and prevent or delay infectability of cells with HIV virus and delay reappearance of the virus in the treated cells. These compositions are also effective against hepatitis and such as herpes, influenza and rhinoviruses and can be used in conjunction with other agents such as other anti-viral compounds or potentiators for the treatment of viral infections.

15 Claims, No Drawings

U.S. PATENT DOCUMENTS

| | | |
|---|---|---|
| 5,149,527 | 9/1992 | Weisenthal . |
| 5,290,801 | 3/1994 | Higley et al. .................... 514/395 |
| 5,310,748 | 5/1994 | Wilde et al. .................... 514/395 |
| 5,329,012 | 7/1994 | Anderson .................... 548/318.5 |
| 5,364,875 | 11/1994 | Wilde .................... 514/375 |
| 5,434,163 | 7/1995 | Edlind et al. .................... 514/310 |
| 5,629,341 | 5/1997 | Camden . |
| 5,656,615 | 8/1997 | Camden . |
| 5,665,713 | 9/1997 | Camden . |
| 5,665,751 | 9/1997 | Camden . |
| 5,767,138 | 6/1998 | Camden . |
| 5,770,616 | 6/1998 | Camden . |
| 5,840,742 | 11/1998 | Camden . |
| 5,854,231 | 12/1998 | Camden . |
| 5,872,142 | 2/1999 | Camden . |
| 5,880,144 * | 3/1999 | Camden .................... 514/397 |
| 5,900,429 | 5/1999 | Camden . |
| 5,902,804 | 5/1999 | Camden . |
| 5,908,855 | 6/1999 | Camden . |
| 5,929,099 | 7/1999 | Camden . |
| 5,932,604 | 8/1999 | Camden . |
| 5,932,609 | 8/1999 | Camden . |
| 6,025,377 | 2/2000 | Camden . |
| 6,077,862 | 6/2000 | Camden . |

OTHER PUBLICATIONS

Lovett, Diss. Abstr. Int., (Sci), vol. 39, No. 11, (1979) pp. 5315–5316.

Brabender, et al., Cancer Research, vol. 36 (Mar., 1976) pp. 905–916.

Atassi et al., Europ., J. Cancer, vol. 11 (1975) pp. 599–607.

Brown, et al., J. Am. Chem. Soc., 83:1764–65 (1961).

Grenda, et al., J. Org. Chem. 30,259 (1965).

W. T. Thompson, Agricultural Chemicals Book IV, Fungicides, pp. 154, 121, 123 (1965).

Carter, W.A. CRC Press, Selective Inhibitors of Viral Functions, pp. 277–346 (1975).

Merck Index, Eighth Edition, 1968, p. 1035.

DuPont, Material Safety Data Sheet Benlate Fungicide, Sep. 27, 1994.

Derwent Publications, AN 95–400884 and Japan Patent Abstracts, JP 07 277956 (1995).

Teicher, et al., Breast Cancer Research and Treatment, vol. 36, No. 2, pp 227–236 (1995).

Bissery, et al., Seminars in Oncology: Management of Breast Cancer: A New Therapeutic Approach, vol. 22, No. 6-S13, pp. 3–16, (1995).

Chemical Abstracts 113:112365 (1990) Ghannoum, et al.

Ram, et al., J. Med. Chem., 35, No. 3, 539–547 (1992).

Nene, et al., International Science Publisher, Fungicides in Plant Disease Control, Chapter 9, 1993.

Private Communication to Dr. Von Hoff from National Institute of Health, National Cancer Society (1995).

Chemical Abstracts 92:123231 (1979) Menzel et al.

Lacey et al., International Journal for Parasitology, vol. 18 No. 7, pp 885–936 (1988).

Merck Index, $12^{th}$ ed., 7943 and 9877, Merck & Co. (NJ 1996).

Chemical Abstracts 102:217569 (1985) Elgebaly et al.

Chemical Abstracts 87:161659 (1997) Lundy et al.

Lacey, et al., Biochemical Pharma., vol. 34, No. 7, pp. 1073–1077 (1985).

Lassnau, et al., Chest, vol. 104, pp 119–122 (1993).

Georgopapadakov et al., Science vol. 264, pp. 371–373 (Apr. 15, 1994).

Carter et al., Chemotherapy of Cancer, $2^{nd}$ Ed., John Wiley & Sons, NY, NY (1981), pp. 362–365.

Chemical Abstracts 98:66765, Vergieva (1998).

Lapras, M., et al., Etude expérimentale des propriétés anticancéreuses potentielles du Parbendazole, Bull. Soc. Sci. Vét et Méd. comparée, Lyon 1975, 77, n 6, with translation.

Chemical Abstracts 65:6570h referring to BE patent, date unknown.

Laparas, M. et al. Bull. Soc. Sci. Vet. et Med. comparee, Lyon, 1975, vol. 77, No. 6, pp. 379–397 (in French)—and English translation thereof.

* cited by examiner

HIV AND VIRAL TREATMENT

This is a continuation in part of U.S. patent application Ser. No. 09/081,384, filed May 19, 1998, now abandoned.

TECHNICAL FIELD

This invention is a method of treating viral infections, notably HIV. The pharmaceutical composition contains one or more benzimidazole derivatives, notably a thiabendazole compound.

BACKGROUND OF THE INVENTION

HIV and other viral infections are one leading cause of death. HIV is a disease in which a virus is replicated in the body which attacks the body's immune system. The HIV virus is not easily destroyed nor is there a good mechanism for keeping the host cells from replicating the virus. Herpes Simplex is another viral infection which is difficult, if not impossible, to cure. A method of treating these diseases and other viral infections is highly desirable. A material which targets the HIV virus and inhibit viral replication is highly desirable.

Several drugs have been approved for treatment of this devastating disease, including azidovudine (AZT), didanosine (dideoxyinosine, ddI), d4T, zalcitabine (dideoxycytosine, ddC), nevirapine, lamivudine (epivir, 3TC), saquinavir (Invirase), ritonavir (Norvir), indinavir (Crixivan), and delavirdine (Rescriptor). See M. I. Johnston & D. F. Hoth, Science, 260(5112), 1286–1293 (1993) and D. D. Richman, Science, 272(5270), 1886–1888 (1996 An AIDS vaccine (Salk's vaccine) has been tested and several proteins which are chemokines from CD8 have been discovered to act as HIV suppressors. In addition to the above synthetic nucleoside analogs, proteins, and antibodies, several plants and substances derived from plants have been found to have in vitro anti-HIV activity. However, HIV virus is not easily destroyed nor is there a good mechanism for keeping the host cells from replicating the virus.

Thus, medical professionals continue to search for drugs that can prevent HIV infections, treat HIV carriers to prevent them from progressing to full-blown deadly AIDS, and treat the AIDS patient.

Herpes simplex virus (HSV) types 1 and 2 are persistent viruses that commonly infect humans; they cause a variety of troubling human diseases. HSV type 1 causes oral "fever blisters" (recurrent herpes labialis), and HSV type 2 causes genital herpes, which has become a major venereal disease in many parts of the world. No fully satisfactory treatment for genital herpes currently exists. In addition, although it is uncommon, HSV can also cause encephalitis, a life-threatening infection of the brain. (The Merck Manual, Holvey, Ed., 1972; Whitley, Herpes Simplex Viruses, In: Virology, 2nd Ed., Raven Press (1990)). A most serious HSV-caused disorder is dendritic keratitis, an eye infection that produces a branched lesion of the cornea, which can in turn lead to permanent scarring and loss of vision. Ocular infections with HSV are a major cause of blindness. HSV is also a virus which is difficult, if not impossible to cure.

Hepatitis is a disease of the human liver. It is manifested with inflammation of the liver and is usually caused by viral infections and sometimes from toxic agents. Hepatitis may progress to liver cirrhosis, liver cancer, and eventually death. Several viruses such as hepatitis A, B, C, D, E and G are known to cause various types of viral hepatitis. Among them, HBV and HCV are the most serious. HBV is a DNA virus with avirion size of 42 nm. HCV is a RNA virus with a virion size of 30–60 nm. See D. S. Chen, J. Formos. Med. Assoc., 95(1), 6–12 (1996).

Hepatitis C infects 4 to 5 times the number of people infected with HIV. Hepatitis C is difficult to treat and it is estimated that there are 500 million people infected with it worldwide (about 15 time those infected with HIV). No effective immunization is currently available, and hepatitis C can only be controlled by other preventive measures such as improvement in hygiene and sanitary conditions and interrupting the route of transmission. At present, the only acceptable treatment for chronic hepatitis C is interferon which requires at least six (6) months of treatment and or ribavarin which can inhibit viral replication in infected cells and also improve liver function in some people. Treatment with interferon with or without Ribavarin however has limited long term efficacy with a response rate about 25%.

Hepatitis B virus infection lead to a wide spectrum of liver injury. Moreover, chronic hepatitis B infection has been linked to the subsequent development of hepatocellular carcinoma, a major cause of death. Current prevention of HBV infection is a hepatitis B vaccination which is therapeutically effective. However, vaccination is not effective in treating those already infected (i.e., carriers and patients). Many drugs have been used in treating chronic hepatitis B and none have been proven to be effective, except interferon.

Treatment of HCV and HBV with interferon has limited success and has frequently been associated with adverse side effects such as fatigue, fever, chills, headache, myalgias, arthralgias, mild alopecia, psychiatric effects and associated disorders, autoimmune phenomena and associated disorders and thyroid dysfunction.

Because the interferon therapy has limited efficacy and frequent adverse effects, a ore effective regimen is needed.

SUMMARY OF THE INVENTION

A pharmaceutical composition for treatment of animals, and in particular, warm blooded animals and humans, comprising a pharmaceutical carrier and an effective amount anti-viral compound selected from the group consisting of:

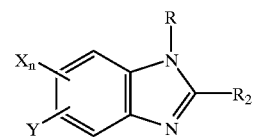

wherein X is hydrogen, halogen, alkyl of less than 7 carbon atoms or alkoxy of less than 7 carbon atoms; n is a positive integer of less than 4; Y is hydrogen, chlorine, nitro, oxychloro, methyl or ethyl; and R is hydrogen, or an alkyl group of from 1 to 8 carbon atoms and $R_2$ is 4-thiazolyl is claimed. Preferably the benzimidazole is substituted with either a chloro (Cl—) or oxychloro (ClO—) in the 5 or 7 position (meta to the bridging carbons of the benzene ring) and the remaining substituents of the benzene ring are hydrogen.

Preferably the compositions are:

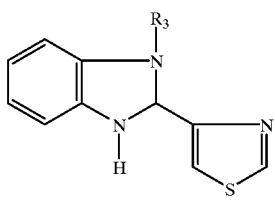

wherein R$_3$ is an alkyl of 1 through 8 carbon atoms and the non-toxic, pharmaceutically acceptable acid addition salts with both organic and inorganic acids. The most preferred compound is 2-(4-thiazolyl)benzimidazole.

The compositions can also be used to treat HIV and other viral infections. The drug can be given daily or from 1 to 4 times a week.

In the present invention it has been discovered that the compounds described above are useful for the inhibition of HIV and the treatment of HIV infection. The present invention also provides methods for the treatment of HIV infection comprising administering to a host infected with HIV a pharmaceutically or therapeutically effective or acceptable amount of a compound as described above, particularly those wherein R is 4-thiazolyl.

More specifically, this invention provides an anti-viral composition comprising a pharmaceutical carrier and a benzimidazole derivative as defined herein along with a method for treating viral infections. These compositions can prevent replication of the HIV virus, create virus resistance in the patient and prevent or delay infectability of cells with HIV virus and delay reappearance of the virus in the treated cells.

These compositions are also effective against viruses and are used to treat viral infections and this invention provides a method of treating viral infections such as herpes, hepatitis, influenza and rhinoviruses.

The compositions can be used in conjunction with other treatments.

DETAILED DESCRIPTION OF TH INVENTION

A. Definitions:

As used herein, the term "comprising" means various components can be conjointly employed in the pharmaceutical composition of this invention. Accordingly, the terms "consisting essentially of" and "consisting of" are embodied in the term comprising.

As used herein, a "pharmaceutically acceptable" component is one that is suitable for use with humans and/or animals without undue adverse side effects (such as toxicity, irritation, and allergic response) commensurate with a reasonable benefit/risk ratio.

As used herein, the term "therapeutically effective amount" refers to the quantity of a component which is sufficient to yield a desired therapeutic response without undue adverse side effects (such as toxicity, irritation, or allergic response) commensurate with a reasonable benefit/risk ratio when used in the manner of this invention. The specific "therapeutically effective amount" will, obviously, vary with such factors as the particular condition being treated, the physical condition of the patient, the type of mammal being treated, the duration of the treatment, the nature of concurrent therapy (if any), and the specific formulations employed and the structure of the compounds or its derivatives. Therapeutically effective amounts are generally recognized as being safe and effective amounts.

As used herein, a "pharmaceutical addition salts" is salt of the anti-viral compound with an organic or inorganic acid.

These preferred acid addition salts are chlorides, bromides, sulfates, nitrates, phosphates, sulfonates, formates, tartrates, maleates, malates, citrates, benzoates, salicylates, ascorbates, and the like.

As used herein, a "pharmaceutical carrier" is a pharmaceutically acceptable solvent, suspending agent or vehicle for delivering the anti-viral agent to the animal or human. The carrier may be liquid or solid and is selected with the planned manner of administration in mind.

As used herein, the "anti-viral compounds" are the benzimidazoles, and their salts. The exact benzimidazoles are described in detail below. The preferred materials are the products sold under the names "thiabendazole®" sold by Merck.

As used herein "viruses" includes viruses which infect animals or mammals, including humans. Viruses includes HIV, influenza, polio viruses, hepatitis, herpes, rhinoviruses, and the like.

As used herein "adjunct therapy" means that the patient in need of the drug is treated or given another drug for the disease in conjunction with the benzimidazole derivatives. This adjunct therapy can be sequential therapy where the patient is treated first with one drug and then the other or the two drugs are given simultaneously.

B. The Anti-Viral Compounds

The anti-viral and anti-viral compounds are benzimidazole derivatives which are known for their antifungal activities. They are systemic fungicides used to prevent and eradicate fungi. They are also used as antihelmitics. The compounds have the following structure:

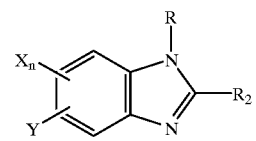

wherein X is hydrogen, halogen, alkyl of less than 7 carbon atoms or alkoxy of less than 7 20 carbon atoms; n is a positive integer of less than 4; Y is hydrogen, chlorine, oxychloro, nitro, hydroxy, methyl or ethyl; and R is hydrogen or an alkyl group of from 1 to 8 carbon atoms and R$_2$ is 4-thiazolyl is claimed. Preferably the benzimidazole is substituted with either a chloro or oxychloro in the 5 position and the remaining substituents of the benzene ring are hydrogen. Preferably the compositions are:

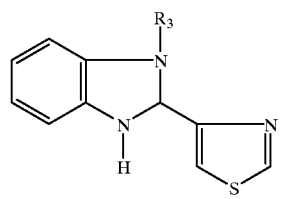

wherein R$_3$ is an alkyl of 1 through 8 carbon atoms and the non-toxic, pharmaceutically acceptable acid addition salts with both organic and inorganic acids. The most preferred compound is 2-(4-thiazolyl)benzimidazole or the non-toxic, pharmaceutically acceptable acid addition salts with both organic and inorganic acids. Suitable acid addition salts are acid addition salts are selected from the group consisting of chlorides, bromides, sulfates, nitrates, phosphates, sulfonates, formates, tartrates, maleates, malates, citrates, benzoates, salicylates, ascorbates and the like.

The benzimidazole compounds also include prodrugs. "Prodrugs" are considered to be any covalently bonded carriers which release the active parent drug according to the formula of the benzimidazole derivatives described above in vivo when such prodrug is administered to a mammalian subject. Prodrugs of the benzimidazole compounds are prepared by modifying functional groups present in the compounds in such a way that the modifications are cleaved, either in routine manipulation or in vivo, to the parent compounds. Prodrugs include compounds wherein hydroxy, amine, or sulfhydryl groups are bonded to any group that, when administered to a mammalian subject, cleaves to form a free hydroxyl, amino, or sulfhydryl group, respectively. Examples of prodrugs include, but are not limited to, acetate, formate, or benzoate derivatives of alcohol and amine functional groups in the benzimidazole derivatives; phosphate esters, dimethylglycine esters, aminoalkylbenzyl esters, aminoalkyl esters and carboxyalkyl esters of alcohol and phenol functional groups in the benzimidazole derivatives; and the like.

The pharmaceutically acceptable salts of the benzimidazole derivatives include the conventional non-toxic salts or the quaternary ammonium salts of the benzimidazole derivatives formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention are synthesized from the benzimidazole derivatives which contain a basic or acidic moiety by conventional chemical methods. Generally, such salts are prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 17th ed., Mack Publishing Company, Easton, Pa., 1985, p. 1418, the disclosure of which is hereby incorporated by reference. The disclosures of all of the references cited herein are hereby incorporated herein by reference in their entirety.

Synthesis

The benzimidazole derivatives are prepared in a number of ways well known to one skilled in the art of organic synthesis. The benzimidazole derivatives are synthesized using the methods described below, together with synthetic methods known in the art of synthetic organic chemistry, or variations thereon as appreciated by those skilled in the art. Preferred methods include but are not limited to those methods described below. Each of the references cited below are hereby incorporated herein by reference.

These compounds are prepared according to the method described in U.S. Pat. No. 3,738,995 issued to Adams et al, Jun. 12, 1973. The thiazolyl derivatives are prepared according to the method described in Brown et al., *J. Am. Chem. Soc.* 83 1764 (1961) and Grenda et al. *J. Org. Chem.*, 30, 259 (1965).

C. Dosage and Dosage Delivery Forms

The type of compound and the carrier and the amount will vary widely depending on the species of animal or human, body weight, and virus or viral infection being treated. The dosage administered will vary depending upon known factors, such as the pharmacodynamic characteristics of the particular agent and its mode and route of administration; the age, health and weight of the recipient; the nature and extent of the symptoms; the kind of concurrent treatment; the frequency of treatment; and the effect desired.

The benzimidazole is preferably micronized or powdered so that it is more easily dispersed and solubilized by the body. Processes for grinding or pulverizing drugs are well known in the art. For example, a hammer mill or similar milling device are used. The preferred particle size is less than about $100\mu$ and preferably less than $50\mu$.

The dosage administered will vary depending upon known factors such as the pharmacodynamic characteristics of the particular active ingredient, and its mode and route of administration; age, sex, health, metabolic rate, absorptive efficiency and/or weight of the recipient; nature and extent of symptoms; kind of concurrent treatment, frequency of treatment; and/or the effect desired.

Dosage forms (compositions) suitable for internal administration contain from about 1.0 milligram to about 5000 milligrams of active ingredient per unit. In these pharmaceutical compositions, the active ingredient will ordinarily be present in an amount of about 0.5–95% by weight based on the total weight of the composition. Based on the body weight of the patient, the dosage may be administered in one or more doses several times per day or per week. Multiple dosage units may be required to achieve a therapeutically effective amount. For example, if the dosage form is 1000 mg, and the patient weighs 40 kg, one pill will provide a dose of 25 mg per kg for that patient. It will provide a dose of only 12.5 mg/kg for a 80 kg patient.

The compounds have shown dose responsiveness in vivo against viruses and cancers in mice at 500 mg/kg, 2500 mg/kg, 3500 mg/kg, 4000 mg/kg, 5000 mg/kg and 6000 mg/kg. Generally a dosage effective in mice translates to about $\frac{1}{12}$ of the dosage required in humans. By way of general guidance, for humans a dosage of as little as about 30 milligrams (mg) per kilogram (kg) of body weight and up to about 10000 mg per kg of body weight is suitable. Preferably from 250 mg/kg to about 5000 mg/kg of body weight is used. Most preferably the doses are between 100 mg/kg to about 3000 mg/kg of body weight. However, a dosage of between about 2 milligrams (mg) per kilogram (kg) of body weight to about 400 mg per kg of body weight is also suitable for some indications.

Intravenously, the most preferred doses may range from about 1 to about 1000 mg/kg/minute during a constant rate infusion. Benzimidazole derivatives may be administered in a single daily dose, or the total daily dosage may be administered in divided doses of two, three, or four times daily. The benzimidazole derivatives are given in one or more doses on a daily basis or from one to three times a week.

The benzimidazole derivatives may also be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittant throughout the dosage regimen.

Generally, the dosage in man is lower than for small warm blooded mammals such as mice. A dosage unit may comprise a single compound or mixtures thereof with other compounds or other viral inhibiting compounds or anti-viral compounds. The dosage unit can also comprise diluents, extenders, carriers and the like. The unit may be in solid or gel form such as pills, tablets, capsules and the like or in liquid form suitable for oral, rectal, topical, intravenous injection or parenteral administration.

The benzimidazole derivatives are typically mixed with a pharmaceutically acceptable carrier. This carrier can be a solid or liquid and the type is generally chosen based on the type of administration being used. The active agent can be coadministered in the form of a tablet or capsule, as an agglomerated powder or in a liquid form. Examples of suitable solid carriers include lactose, sucrose, gelatin and agar. Capsule or tablets are easily formulated and can be made easy to swallow or chew; other solid forms include granules, and bulk powders. Tablets may contain suitable binders, lubricants, diluents, disintegrating agents, coloring agents, flavoring agents, flow-inducing agents, and melting agents. Examples of suitable liquid dosage forms include solutions or suspensions in water, pharmaceutically acceptable fats and oils, alcohols or other organic solvents, including esters, emulsions, syrups or elixirs, suspensions, solutions and/or suspensions reconstituted from non-effervescent granules and effervescent preparations reconstituted from effervescent granules. Such liquid dosage forms may contain, for example, suitable solvents, preservatives, emulsifying agents, suspending agents, diluents, sweeteners, thickeners, and melting agents. Oral dosage forms optionally contain flavorants and coloring agents. Parenteral and intravenous forms would also include minerals and other materials to make them compatible with the type of injection or delivery system chosen.

Examples of Formulation

The benzimidazole derivatives of this invention are administered as treatment for viral infections, including retroviral, by any means that produces contact of the active agent with the agent's site of action in the body. The anti-viral compounds (active ingredients) of this invention are administered to inhibit virus growth or viral infections by any means that produces contact of the active ingredient with the agent's site of action in the body of a mammal or animal. They can be administered by any conventional means available for use in conjunction with pharmaceuticals, either as individual therapeutic agents or in a combination of therapeutic agents. They can be administered alone, but generally are administered with a pharmaceutical carrier selected on the basis of the chosen route of administration and standard pharmaceutical practice.

The benzimidazole derivatives are administered in oral dosage forms as tablets, capsules (each of which includes sustained release or timed release formulations), pills, powders, granules, elixirs, tinctures, suspensions, syrups, and emulsions. The benzimidazole derivatives may also be administered in intravenous (bolus or infusion), intraperitoneal, subcutaneous, or intramuscular form, all using dosage forms well known to those of ordinary skill in the pharmaceutical arts.

In the methods of the present invention, the compounds herein described in detail can form the active ingredient, and are typically administered in admixture with suitable pharmaceutical diluents, excipients, or carriers (collectively referred to herein as a pharmaceutically acceptable carrier or carrier materials) suitably selected with respect to the intended form of administration, that is, oral tablets, capsules, elixirs, syrups and the like, and consistent with conventional pharmaceutical practices.

For instance, for oral administration in the dosage unit form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like. For oral administration in liquid dosage form, the oral drug components are combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The benzimidazole derivatives can also be administered in the form of liposome delivery systems, such as small unilamellar vesicles, large unilamallar vesicles, and multilamellar vesicles. Liposomes can be formed from a variety of phospholipids, such as cholesterol, stearylamine, or phosphatidylcholines.

Benzimidazole derivatives may also be coupled with soluble polymers as targetable drug carriers. Such polymers can include polyvinylpyrrolidone, pyran copolymer, polyhydroxylpropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

The active ingredient can be administered orally in solid dosage forms, such as capsules, tablets, and powders, or in liquid dosage forms, such as elixirs, syrups, and suspensions. It can also be administered parentally, in sterile liquid dosage forms.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance. In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol. Suitable pharmaceutical carriers are described in Remington's Pharmaceutical Sciences, Mack Publishing Company, a standard reference text in this field.

Useful pharmaceutical dosage forms for administration of the compounds of this invention are illustrated as follows:

Capsules

A large number of unit capsules are prepared by filling standard two-piece hard gelatin capsules each with 100 to 500 milligrams of powdered active ingredient, 5–150 milligrams of lactose, 5–50 milligrams of cellulose, and 6 milligrams magnesium stearate.

Soft Gelatin Capsules

A mixture of active ingredient in a digestible oil such as soybean oil, cottonseed oil or olive oil is prepared and injected by means of a positive displacement pump into gelatin to form soft gelatin capsules containing 100–500 milligrams of the active ingredient. The capsules are washed and dried.

Tablets

A large number of tablets are prepared by conventional procedures so that the dosage unit was 100–500 milligrams of active ingredient, 0.2 milligrams of colloidal silicon dioxide, 5 milligrams of magnesium stearate, 50–275 milligrams of microcrystalline cellulose, 11 milligrams of starch and 98.8 milligrams of lactose. Appropriate coatings may be applied to increase palatability or delay absorption.

Injectable

A parenteral composition suitable for administration by injection is prepared by stirring 1.5% by weight of active ingredient in 10% by volume propylene glycol and water. The solution is made isotonic with sodium chloride and sterilized.

Suspension

An aqueous suspension is prepared for oral administration so that each 5 ml contain 100 mg of finely divided active ingredient, 200 mg of sodium carboxymethyl cellulose, 5 mg of sodium benzoate, 1.0 g of sorbitol solution, U.S.P., and 0.025 ml of vanillin.

The present invention also includes pharmaceutical kits useful, for example, for the treatment of HIV infection, which comprise one or more containers containing a pharmaceutical composition comprising a therapeutically effective amount of a benzimidazole derivative. Such kits may further include, if desired, one or more of various conventional pharmaceutical kit components, such as, for example, containers with one or more pharmaceutically acceptable carriers, additional containers, etc., as will be readily apparent to those skilled in the art. Printed instructions, either as inserts or as labels, indicating quantities of the components to be administered, guidelines for administration, and/or guidelines for mixing the components, may also be included in the kit. In the present disclosure it should be understood that the specified materials and conditions are important in practicing the invention but that unspecified materials and conditions are not excluded so long as they do not prevent the benefits of the invention from being realized.

One or more benizmidazoles can be used in a single treatment. The benzimidazoles can be combined with other anti-viral agents or potentiators. Potentiators are materials which affect the body's response to the anti-viral agent. In the case of HIV an adjunct therapy with AZT, TC-3 or the protease inhibitors is preferred.

D. Adjunct Therapy

One or more benzimidazole derivatives can be combined with other antiviral agents or potentiators. Potentiators are materials which affect the body's response to the anti-viral agent. In the case of HIV an adjunct therapy with AZT, TC-3 or protease inhibitors is effective. In the case of hepatitis, cyclovir, famciclovir or valacyclovir, Ribavirin, interferon or combinations of Ribavirin and Interferon or beta globulin is administered as an adjunct therapy. For herpes, a recombinant alpha interferon can be used.

The adjunct therapy can be sequential, that is the treatment with one agent first and then the second agent, or it can be treatment with both agents at the same time. The sequential therapy can be within a reasonable time after the completion of the first therapy before beginning the second therapy. The treatment with both agents at the same time can be in the same daily dose or in separate doses. For example treatment with one agent on day 1 and the other on day 2. The exact regimen will depend on the disease being treated, the severity of the infection and the response to the treatment.

E. Method of Treatment

The method of treatment can be any suitable method which is effective in the treatment of the particular virus type that is being treated. Treatment may be oral, rectal, topical, parenteral or intravenous administration and the like. The method of applying an effective amount also varies depending on the virus or viral infection being treated. It is believed that parenteral treatment by intravenous, subcutaneous, or intramuscular application of the benzimidazole compounds, formulated with an appropriate carrier, additional viral inhibiting compound or compounds or diluent to facilitate application will be the preferred method of administering the compounds to warm blooded animals.

The method of treating viral infections may also be by oral, rectal, topical, parenteral or intravenous administration. The actual time and dosage will depend on the virus being treated and the desired blood levels.

The following examples are illustrative and are not meant to be limiting to the invention.

The following examples illustrate the effectiveness of thiabendazole, 2-(4-thiazolyl)-1H-benzimidazole, against HIV and the benzimidazoles derivatives against a number of viruses.

Thiabendazole is effective at totally suppressing virus production in chronically infected cells. The extra cellular viral count goes effectively to zero or non-detectable levels. Thiabendazole does not kill the chronically infected cells though it does reduce the rate of cell proliferation at active concentrations. Thiabendazole does not affect $CD_4$ expression in uninfected cells. At effective concentrations thiabendazole slows but does not alter the normal cellular RNA or protein synthesis of either infected or non-infected cells. Thiabendazole is effective in a variety of chronically infected cell types (this effect is not cell type specific.)

Thiabendazole is effective against a variety of HIV virus strains. (Not virus strain specific—although some variance by strain is observed; SK-1>IIIB>RF) Also thiabendazole is not effective on SIV in vitro or in vivo.

After 20 months no resistant virus strains to thiabendazole have developed in tests designed to do so. Resistance develops in six months or less in this test for existing HIV drugs with resistance strains for protease inhibitors developing in about 3–4 months.

Thiabendazole does not adversely affect the activity of existing HIV drugs, AZT, 3TC, ddC, ddI or protease inhibitors (saquinavir and indinavir) in acutely infected cells, nor do any of these existing drugs interfere with the efficacy of thiabendazole in chronically infected cells. It is used in combination with these drugs. Thiabendazole is also effective against protease inhibitor resistant viruses.

Thiabendazole confers temporary suppression of viral production from 4 to 80 days after treatment stops. This is unique and a useful feature whenever one has problems with compliance.

The results of these studies are summarized in detail below:

EXAMPLE 1

HIV Testing
HIV Virus Replication Study

Thiabendazole was tested in chronically infected HIV virus. These cell populations contain integrated copies of the HIV genome and constitutively produce HIV at relatively high levels (CEM-SK1, U937-SKI and H9-SK1 from Frederick Research Center, Maryland) or are latently infected and only produce virus after stimulation with phorbol esters, tumor necrosis factor or IL6 (U1 and ACH2). Virus products was reduced in all cell lines tested and the compounds did not stimulate virus production form the latently infected cells. Reductions in virus production were observed when quantifying supernatant reverse transcriptase activity, supernatant p24 as well as intracellular p24, indicating the compounds inhibit virus production at a step of replication prior to production of intracellular proteins.

Quantification of the infectivity of virions produced from the infected cells demonstrates reductions in the number of infectious virions in parallel with reductions in supernatant RT or p24, indicating that the compounds reduce the amount of virus produced, but not the quality of the virions. Inhibition of virus production from the chronically infected cells was observed at concentrations which were nontoxic to the target class. Thiabendazole inhibited virus production at concentrations great than 1–10 $\mu$g/ml.

Toxicity to the chronically infected cells was similar to that observed with the uninfected cells. Evaluation of thiabendazole on chronically infected cells was performed by evaluation of thymidine (DNA), uridine (RNA) and leucine (protein) incorporation into cellular macromolecules. Inhibition of cellular macromolecule synthesis paralleled the toxicity of the tow compounds as would be expected and did not occur at lower nontoxic concentrations found to inhibit virus production from the chronically infected cells.

After 28 days of treatment with these compounds on chronically infected cells, the toxicity of the compounds to the target cells appeared similar in both uninfected and chronically infected cells. The compounds do not preferentially kill HIV-infected cells. Reductions in the level of virus production were stable and were observed at concentration greater than 10 $\mu$g/ml for thiabendazole.

These results suggest that thiabendazole can quickly reduce the level of virus production from cell populations chronically infected with HIV-1 and the antiviral effect is maintained with prolonged compound exposure. This reduction of virus production occurs at concentrations which are nontoxic to the host cell and which have no effect on the synthesis of cellular DNA, RNA and protein.

Virus Resistance Studies

Chronically infected HIV cells were cultured in the presence of thiabendazole at 1 $\mu$g/ml for the first month, 5 $\mu$g/ml for month two, 10 $\mu$g/ml for the third month, 20 and 40 $\mu$g/ml for the fourth month and 80 $\mu$g/ml for the fifth and sixth months. At the end of each month, the cells were evaluated for virus production compared to chronically infected cells not treated with the compounds. For each of the six months of treatment experience, no change in the antiviral effect was noticed and the toxicity of remains identical. Thiabendazole remains active against HIV and that resistance was not rapidly achieved via the selection of resistant viruses or adaptation of the cells to prevent compound induced toxicity. Virus production remains totally suppressed from cultures treated with thiabendazole at 40 and 80 $\mu$g/ml.

Reappearance of Virus Production from Chronically Infected Cells Previously Treated Chronically infected cells which were treated with compound for prolonged periods were washed free of compound and cultured to determine if, and when, virus production would resume. Cultures in which treatment resulted in the total elimination of virus production were used in these assays. These cultures included chronically infected cells cultured in the presence of 20, 40, and 80 $\mu$g/ml of thiabendazole. Within 4 days virus production resumed from the cells cultured in the presence of the lower concentrations of each compound (20 $\mu$g/ml and 4 $\mu$g/ml). Virus production resumed at the 40 $\mu$g/ml concentration of thiabendazole by day 12. At the highest concentrations virus production was observed at approximately day 70.

Infectability of Cells Treated with Thiabendazole

Cells which were pretreated with thiabendazole for a long period of time were washed free of compound and used as a target cell population. The cells were split into 3 populations and labeled Group 1,2 or 3. Group I was treated with the compound for 24 hours (at the same concentration used in the prolonged treatment phase), washed free of compound and cultured in the presence of infectious virus and fresh compound. Group 2 was pretreated for 24 hours, washed free of compound and cultured in the presence of infectious virus only. Group 3 was cultured for both the pretreatment and the infection phases in fresh medium only (no virus or compound). Virus production from the cell populations was identical irrespective of the culture conditions. These results indicate that the chronically infected cells treated for prolonged periods were not super infected with HIV.

These same benzimidazole derivatives are effective against viruses including other types of HIV, influenza, rhinoviruses and herpes viruses.

Additional Chronic HIV studies

Chronic HIV-1 infected cells U1 were derived from an acute HIV-1 infection of the promonocytic cell line, U937. The chronic HIV-1 infected cells, ACH-2 were derived from an acute HIV-1 infection of the T cell line, A3.01.

These cells were cultured in medium and the phorbol ester, PMA. PMA causes the cells (both U1 and ACH-2) to be activated and not divide but it also causes the U-1 cells to differentiate. This results in fewer cells in the PMA-treated cultures than the media alone cultures. Cell viability was measured when these cell lines were treated with the test compound.

Both cell lines constituitively produce a small amount of HIV-1. ACH-2 cell lines tend to produce more HIV-1 than U1 cells as shown by p-24 ELISA. When either cell line is cultured in the presence of PMA there is an increase in the quantity of HIV-1 produced as measured by the p-24 antigen ELISA.

In addition, the number of institute positive HIV mRNA expressing cells per microscopic field is measured. Comparisons can be made from these numbers since the same number of cells were adhered to the glass slides for each drug concentration ($10 \times 10^6$ cells/ml).

These cells were treated with test samples. Thiabendazole at 60 $\mu$g/ml suppressed replication in the HIV monocytes by 74% and the T-cell HIV replication was increased by 26%. The positive control was interferon which suppressed HIV monocytes replication by 80%. AZT showed no activity in this model.

2-(Methoxycarbonylamino)benzimidazole suppressed replication in the HIV monocytes by 9% and the T-cell HIV replication was increased by 44%. The positive control was interferon which suppressed HIV monocytes replication by 80% and suppressed T-cell HIV replication by 60%.

Acute HIV Testing

In an in vitro acute model for HIV 2-(methoxycarbonylamino)benzimidazole inhibited viral replication by 100% at 4 μg/ml and AZT inhibited viral replication by 98% at 1 μg/ml. 2-(4-thiazolyl)-1H-benzimidazole inhibited viral replication by 98% at 60 μg/ml.

The therapeutic index (TI), the ratio of the toxic dose of drug to efficacious dose of drug for 2-(4-thiazolyl)-1H-benzimidazole is 2.8 versus 12, 500 for AZT. The TI for 2-(methoxycarbonylamino)benzimidazole is 1.8.

In Vivo Herpes

In an in vivo herpes screening test of 2-(4-thiazolyl)-1H-benzimidazole at a dose of 200 mg/kg dose, 10% of the mice survived with a 10.4 mean death date; at 100 mg/kg dose 50% of the mice survived with a 9.2 mean death date. The positive control was acyclovir at 75 mg/kg dose; 60% of the mice survived with a mean death date of 17.2 days. In the same test 2-(methoxycarbonylamino)benzimidazole showed no activity.

Other Tests

Both 2-(4-thiazolyl)-1H-benzimidazole and 2-(methoxycarbonylamino) benzimidazole were tested in an in vitro influenza model and showed no activity.

In an in vivo model for influenza 2-(4-thiazolyl)-1H-benzimidazole was tested at 200 mg/kg, 67% of the mice survived with a mean death date of 8 days; at 100 mg/kg, 62% survived with a mean death date of 8.7 days. The positive control was amantadine (75 mg/kg) with 100% of the mice surviving for 21 days. 2-(Methoxycarbonylamino) benzimidazole was not active in the same test.

Both 2-(4-thiazolyl)-1H-benzimidazole and 2-(methoxycarbonylamino) benzimidazole were tested in an in vitro herpes model and showed no activity.

Both 2-(4-thiazolyl)-1H-benzimidazole and 2-(methoxycarbonylamino) benzimidazole were tested in an in vitro rhinovirus model and compared to A-36683. The therapeutic index (TI), the ratio of the toxic dose of drug to efficacious dose of drug, for 2-(4-thiazolyl)-1H-benzimidazole is 1–2 and for 2-(methoxycarbonylamino) benzimidazole is 1–3 versus 1000–3200 for A-36683.

What is claimed is:

1. A method of suppressing HIV virus production in a subject in need thereof comprising administering to the subject a therapeutically effective amount of a benzimidazole of the formula:

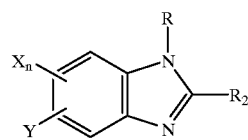

wherein
X is hydrogen, halogen, alkyl of less than 7 carbon atoms or alkoxy of less than 7 carbon atoms;
n is a positive integer of less than 4;
Y is hydrogen, chlorine, nitro, oxychloro, methyl or ethyl;
R is hydrogen or an alkyl group having from 1 to 8 carbon atoms, and
$R_2$ is 4-thiazolyl;
a pharmaceutically acceptable salt thereof, or a prodrug thereof; and a pharmaceutical carrier.

2. A method according to claim 1 wherein the benzimidazole is administered in an amount of 100 mg to 6000 mg and the benzimidazole has the formula:

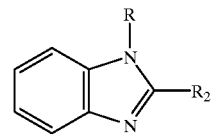

wherein
R is hydrogen or alkyl group having from 1 to 8 carbon atoms, and
$R_2$ is 4-thiazolyl.

3. A method according to claim 2 wherein said benzimidazole is selected from the group consisting of 2-(4-thiazolyl)benzimidazole, and pharmaceutically acceptable salts thereof; and wherein from 1000 mg to 5000 mg of said benzimidazole is administered.

4. A method according to claim 3 wherein said pharmaceutically acceptable salt is selected from the group consisting of chlorides, bromides, sulfates, nitrates, phosphates, sulfonates, formates, tartrates, maleates, malates, citrates, benzoates, salicylates, ascorbates and mixtures thereof.

5. The method of claim 1 wherein the subject is resistant to a protease inhibitor.

6. The method of claim 5 wherein the protease inhibitor is saquinavir.

7. The method of claim 5 wherein the protease inhibitor is indinavir.

8. The method of claim 1 further comprising the step of stopping the administering of the benzimidazole wherein HIV virus production continues to be suppressed.

9. A method of suppressing HIV virus production in a subject in need thereof comprising administering to the subject a therapeutically effective amount of 2-(4-thiazolyl) benzimidazole.

10. The method of claim 9 wherein the subject is resistant to a protease inhibitor.

11. The method of claim 10 wherein the protease inhibitor is saquinavir.

12. The method of claim 10 wherein the protease inhibitor is indinavir.

13. The method of claim 9 further comprising the step of stopping the administering of the benzimidazole wherein HIV virus production continues to be suppressed.

14. A method of treating hepatitis in a subject in need thereof comprising administering to the subject a therapeutically effective amount of a benzimidazole of the formula:

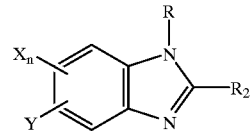

wherein
X is hydrogen, halogen, alkyl of less than 7 carbon atoms or alkoxy of less than 7 carbon atoms;
n is a positive integer of less than 4;

Y is hydrogen, chlorine, nitro, oxychloro, methyl or ethyl;

R is hydrogen or an alkyl group having from 1 to 8 carbon atoms; and $R_2$ is 4-thiazolyl;

a pharmaceutically acceptable salt thereof or a prodrug thereof; and a pharmaceutical carrier.

15. A method of treating hepatitis in a subject in need thereof comprising administering to the subject a therapeutically effective amount of 2-(4-thiazolyl)benzimidazole.

* * * * *